(12) United States Patent  
Steiner

(10) Patent No.: US 7,309,356 B2
(45) Date of Patent: *Dec. 18, 2007

(54) BONE-TENDON- BONE ASSEMBLY WITH CANCELLOUS ALLOGRAFT BONE BLOCK

(75) Inventor: Anton J. Steiner, Wharton, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 626 days.

This patent is subject to a terminal disclaimer.

(21) Appl. No.: 10/637,577

(22) Filed: Aug. 11, 2003

(65) Prior Publication Data

US 2004/0030385 A1  Feb. 12, 2004

Related U.S. Application Data

(63) Continuation-in-part of application No. 10/277,838, filed on Oct. 23, 2002, now Pat. No. 6,730,124, which is a continuation-in-part of application No. 10/092,537, filed on Mar. 8, 2002, now Pat. No. 6,890,354.

(51) Int. Cl.
*A61F 2/08* (2006.01)

(52) U.S. Cl. .............................. 623/13.14; 623/13.17; 623/13.2

(58) Field of Classification Search ............. 623/13.11, 623/13.12, 13.13, 13.14, 13.15, 13.16, 13.17, 623/13.18, 13.19, 13.2
See application file for complete search history.

(56) References Cited

U.S. PATENT DOCUMENTS

| | | | |
|---|---|---|---|
| 4,400,833 A | 8/1983 | Kurland | |
| 4,755,593 A | 7/1988 | Lauren | |
| 5,562,669 A | 10/1996 | McGuire | |
| 5,585,116 A | 12/1996 | Boniface et al. | |
| 5,609,636 A | 3/1997 | Kohrs et al. | |
| 5,632,748 A | 5/1997 | Beck, Jr. et al. | |
| 5,782,919 A | 7/1998 | Zdeblick et al. | |
| 5,972,368 A | 10/1999 | McKay | |
| 5,984,966 A | 11/1999 | Kiema et al. | |
| 5,984,967 A | 11/1999 | Zdeblick et al. | |
| 6,102,948 A | 8/2000 | Brosnahan et al. | |
| 6,245,108 B1 | 6/2001 | Biscup | |
| 6,264,694 B1 | 7/2001 | Weiler | |
| 6,730,124 B2 * | 5/2004 | Steiner | 623/13.14 |

FOREIGN PATENT DOCUMENTS

| | | |
|---|---|---|
| FR | 2582517 | 12/1986 |
| FR | 2582518 | 12/1986 |
| WO | WO 84/03036 | 8/1984 |

* cited by examiner

*Primary Examiner*—Thomas J. Sweet
(74) *Attorney, Agent, or Firm*—John S. Hale; Gipple & Hale

(57) ABSTRACT

The invention is directed toward a bone-tendon-bone assembly extended between two shaped cancellous bone blocks and a method of inserting same in a joint. Each substantially cylindrically shaped cancellous bone block has a central through going bore, a flat exterior longitudinal surface and a channel longitudinally cut in the exterior of the bone block body opposite the flat longitudinal surface. A tendon replacement member is inserted through the central through going bore around the end of each block and looped back along the flat longitudinal side with each block being in a reversed orientation position as to the other block. A channel cut in the exterior surface of each block is adapted to receive an interference screw to keep the block anchored in a bone tunnel previously cut in the respective bones of a joint.

35 Claims, 2 Drawing Sheets

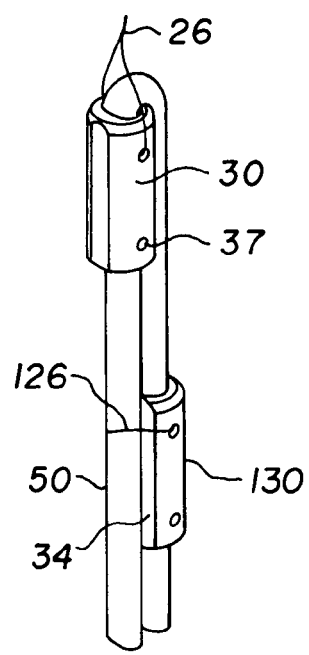
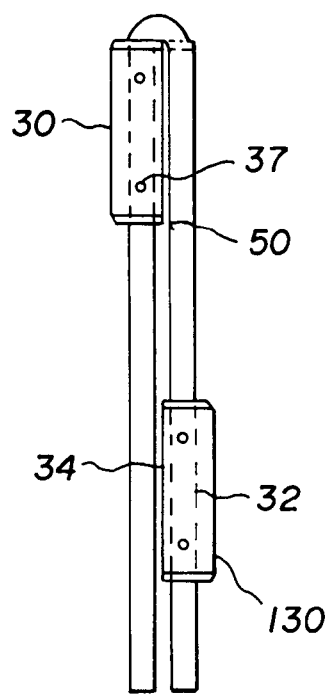
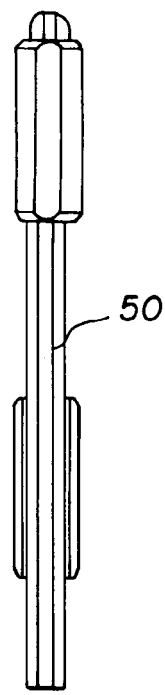
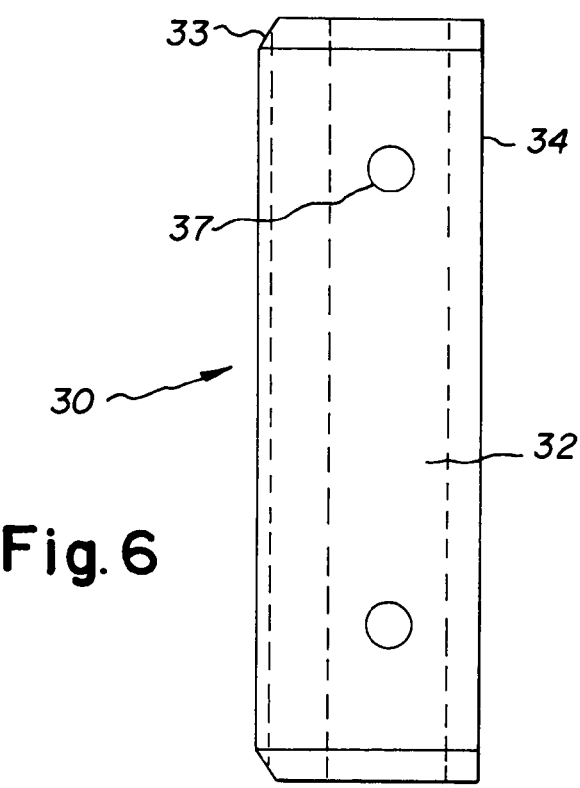
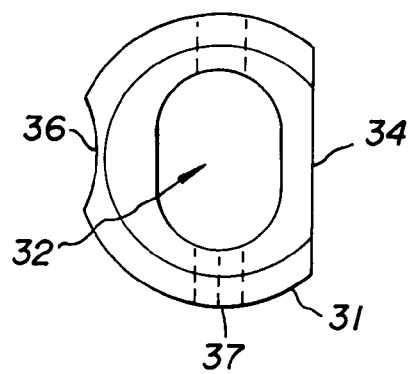
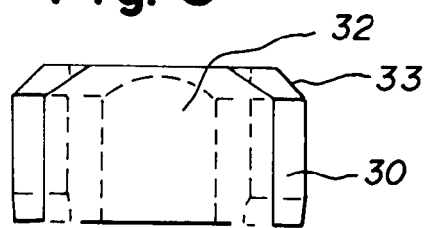

BONE-TENDON-BONE ASSEMBLY WITH CANCELLOUS ALLOGRAFT BONE BLOCK

RELATED APPLICATION

The present application is a continuation-in-part of U.S. patent application Ser. No. 10/277,838 filed Oct. 23, 2002 now U.S. Pat. No. 6,730,124 which is a continuation-in-part of U.S. patent application Ser. No. 10/092,537 filed Mar. 8, 2002 now U.S. Pat. No 6,890,354.

FIELD OF INVENTION

The present invention is generally directed toward a surgical implant product and more specifically is a shaped allograft cancellous bone block implant assembly.

BACKGROUND OF THE INVENTION

Failed ligaments, such as the anterior or posterior cruciate ligaments in the knee joint, significantly limit physical activity and potentially cause chronic knee problems. The anterior cruciate ligament (hereinafter ACL) and the posterior cruciate ligament (PCL) to a lesser extent are often torn during sports related injuries or as result of traumatic stresses. Ligament reconstruction with allograft and autograft tissue has been shown to improve joint function and provide long term improvement in restoration of physical activity. A common surgical method of repair of an ACL is harvesting a patient's patellar tendon with bone blocks from the tibia and patella. The bone-patellar tendon-bone implant offers several advantages, including high initial tensile strength, stiffness, proper length, rigid fixation and direct bone-to-bone incorporation.

The ACL of the knee functions to resist anterior displacement of the tibia from the femur at all flexion positions. The ACL also resists hyper-extension and contributes to rotational stability of the fully extended knee during internal and external tibial rotation. The ACL may also play a role in proprioception. Structurally, the ACL attaches to a depression in the front of the intercondylar eminence of the tibia extending poster-superiorly to the medial wall of the lateral femoral condyle. Partial or complete tears of the ACL are very common, comprising about 100,000 outpatient procedures in the U.S. each year. The preferred treatment of the torn ACL is ligament reconstruction, using a bone-ligament-bone autograft. Cruciate ligament reconstruction has the advantage of immediate stability and a potential for immediate vigorous rehabilitation. However, the disadvantages to ACL reconstruction are significant: for example, normal anatomy is disrupted when the patellar tendon or hamstring tendons of the patient are used for the reconstruction; placement of intraarticular hardware is required for ligament fixation; and anterior knee pain frequently occurs. Moreover, recent reviews of cruciate ligament reconstruction indicate an increased risk of degenerative arthritis with intraarticular ACL reconstruction in large groups of patients.

A second method of treating ACL injuries, referred to as "primary repair", involves suturing the torn structure back into place. Primary repair has the potential advantages of a limited arthroscopic approach, minimal disruption of normal anatomy, and an out-patient procedure under a local anesthetic. The potential disadvantage of primary cruciate ligament repair is the perception that over the long term, ACL repairs do not provide stability in a sufficient number of patients, and that subsequent reconstruction may be required at a later date. The success rate of such anterior cruciate ligament repair has generally hovered in the 60% to 70% range.

The autogenous patellar tendon is an excellent tendon replacement source, providing proper tendon length and bone blocks that are fully osteointegrated without immunological rejection. Unfortunately harvesting autogenous bone-tendon-bone (hereinafter B-T-B) also has a number of adverse effects, including donor morbidity (pain), patellar fracture, tendon rupture and degeneration of the patellofemoral articular surface. As an alternate to autogenous graft tissue, synthetic materials have previously received FDA approval. In this regard polyester braids, steel wire and PTFE (GORE-TEX) have been used surgically. All of these materials have failed to integrate into the bone resulting in the tendon's inability to sustain the tensile and torsional loads applied to the knee in normal usage. Nearly all of these synthetic repairs have been revised with autogenous and/or allograft tissue.

There is a limited supply of allograft bone-patellar tendon-bone (B-PT-B) tissue due in large part to the number of donors that qualify according to the selective donor acceptance criteria. As a result of the limited number of available grafts there is a demand for such grafts which exceeds supply.

The use of substitute bone tissue dates back around 1800. Since that time, research efforts have been undertaken toward the use of materials which are close to bone in composition to facilitate integration of bone grafts. Development has taken place in the use of grafts of a mineral nature such as corals, hydroxyapatites, ceramics or synthetic materials such as biodegradable polymer materials. Surgical implants should be designed to be biocompatible in order to successfully perform their intended function. Biocompatibility may be defined as the characteristic of an implant acting in such a way as to allow its therapeutic function to be manifested without secondary adverse affects such as toxicity, foreign body reaction or cellular disruption.

Human allograft tissue is widely used in orthopaedic, neuro-, maxillofacial, podiatric and dental surgery. The tissue is valuable because it is strong, biointegrates in time with the recipient patient's tissue and can be shaped either by the surgeon to fit the specific surgical defect or shaped commercially in a manufacturing environment. Contrasted to most synthetic absorbable or nonabsorbable polymers or metals, allograft tissue is biocompatible and integrates with the surrounding tissues. Allograft bone occurs in two basic forms; cancellous and cortical. Cancellous bone is a less dense structure than that of cortical bone and is also comprised of triple helix strands of collagen fiber, reinforced with hydroxyapatite. The cancellous bone includes void areas with the collagen fiber component contributing in part to torsional and tensile strength.

Many devices of varying shapes and forms are fabricated from allograft cortical tissue by machining. Surgical implants such as pins, rods, screws, anchors, plates, intervertebral spacers and the like have been made and used successfully in human surgery. These pre-engineered shapes are used by the surgeon in surgery to restore defects in bone to the bone's original anatomical shape. At the present time cancellous bone has not been commercially used for shaped devices which are subject to pull out forces.

Allograft bone is a logical substitute for autologous bone. It is readily available and precludes the surgical complications and patient morbidity associated with obtaining autologous bone as noted above. Allograft bone is essentially a collagen fiber reinforced hydroxyapatite matrix containing active bone morphogenic proteins (BMP) and can be provided in a sterile form. The demineralized form of allograft bone is naturally both osteoinductive and osteoconductive. The demineralized allograft bone tissue is fully incorporated in the patient's tissue by a well established biological mechanism. It has been used for many years in bone surgery to fill the osseous defects previously discussed.

U.S. Pat. No. 5,972,368 issued on Oct. 26, 1999 discloses the use of cortical constructs (e.g. a cortical dowel for spinal fusion) which are cleaned to remove all of the cellular material, fat, free collagen and non-collagenous protein leaving structural or bound collagen which is associated with bone mineral to form the trabecular struts of bone. The shaped bone is processed to remove associated non-collagenous bone proteins while maintaining native bound collagen materials and naturally associated bone minerals. The surface of a machined cortical bone surface is characterized by a wide variety of openings resulting from exposure by the machining process of the Haversian canals present throughout cortical bone. These canals serve to tansport fluids throughout the bone to facilitate the biochemical processes occurring within the bone. They occur at variable angles and depths within the bone.

In French Patent Applications Numbers 2,582,517 and 2,582,518 fragments of bones taken from animals, primarily cattle were partially demineralized and tanned with glutaraldehyde. The bone elements to be implanted were cut to the desired shape from an ox bone which has been subjected to a treatment comprising a degreasing step with an organic solvent such as ethanol, a demineralization step with a calcium extraction agent such as hydrochloric acid and tanning with glutaraldehyde and subsequent washings. Similar demineralization of bone is shown in U.S. Pat. No. 5,585,116 issued Dec. 17, 1996 where partial demineralization is used to facilitate integration of a bone graft. This is accordingly followed by different complementary steps which are intended either to deproteinize the bone completely or to act on the nature of the proteins which then remain linked within the bone matrix or else to increase the proportion of proteins.

Much of the structure and many of the properties of original tissues may be retained in transplants through use of xenogeneic or heterograft materials, that is, tissue from a different species than the graft recipient. For example, tendons or ligaments from cows or other animals have been covered with a synthetic mesh and were transplanted into a heterologous host in U.S. Pat. No. 4,400,833. Flat tissues such as pig pericardia are also disclosed as being suitable for heterologous transplantation in U.S. Pat. No. 4,400,833. Bovine peritoneum fabricated into a biomaterial suitable for prosthetic heart valves, vascular grafts, burn and other wound dressings is disclosed in U.S. Pat. No. 4,755,593. Bovine, ovine, or porcine blood vessel heterografts are disclosed in WO 84/03036. However, none of these disclosures describe the use of a xenograft for ACL replacement.

Xenograft materials must be chemically treated to reduce immunogenicity prior to implantation into a recipient. For example, glutaraldehyde is used to cross-link or "tan" xenograft tissue in order to reduce its antigenicity, as described in detail in U.S. Pat. No. 4,755,593. Other agents such as aliphatic and aromatic diamine compounds may provide additional cross linking through the side chain carboxyl groups of aspartic and glutamic acid residues of the collagen polypeptide. Glutaraldehyde and diamine tanning also increases the stability of the xenograft tissue.

U.S. Pat. No. 5,562,669 issued Oct. 8, 1996 discloses a B-T-B tendon anchor device using autologus bone plugs taken from the cores drilled out from the bone tunnels of the patient or alternatively donor bone, namely allograft bone to make the bone plugs. The linear cylindrical plug member is provided with two longitudinal substantially parallel grooves cut on opposite sides of each bone plug which provide a recess in which the tendon can be seated. A notch may also be drilled if desired across one end of the bone plug so that the tendon can be wrapped alongside and around the end of the bone plug without protruding excessively from the plug. Suture holes can be cut through the bone plug for attaching the tendon to the plug as is shown in FIGS. 4a and 4b. The perfectly symmetric pattern of the '669 device presents the tendon equally on both sides of the bone block.

Likewise U.S. Pat. No. 5,632,748 issued May 27, 1997 discloses a B-T-B tendon anchor device formed of plastic, bone, stainless steel or any other suitable material. The body is tapered and formed with a groove to receive a fixation screw and two curved recesses to hold a tendon which is looped over the device. The fixation groove is provided with threads (FIG. 3) and the tendon grooves are provided with teeth. (FIG. 4). A two piece version having a tongue and groove and stepped mating faces for joinder with two tendon grooves is shown in FIG. 7.

U.S. Pat. No. 6,264,694 issued Jul. 24, 2001 discloses a spherical member having a through going bore and parallel recessed surfaces which enable it to be tied to the end of a soft tissue ligament graft to allow the graft to be secured within the bone tunnel by an interference screw.

Presently, the bone block systems in B-T-B grafts have been made from cortical bone or synthetic materials. Cancellous bone has not been used for bone tendon bone assemblies because of concerns with strength and screw pullout.

SUMMARY OF THE INVENTION

The present invention is directed to a bone-tendon-bone composite graft of novel construction for use in tendon and cruciate ligament reconstruction using cancellous bone for the bone block, positioning one bone block on adjacent tendons. In the inventive surgical installation, a bone tunnel is drilled in each of two bones of the joint. The allograft cancellous bone blocks are pre-machined to form an oblong or oval central through going bore, a longitudinal channel which is parallel to the axis of the central bore and a planar surface cut longitudinally in the exterior surface of the bone block. At least one tendon replacement member, such as a semitendinous, tibialis or gracilis tendon or a combination of tendons is extended between the bone blocks through the central bore of each bone block and over an end of the bone block and back along the longitudinal planar surface formed on the outer surface of each bone block. Each bone block is inserted into one of the bone tunnels of the femur and the tibia and adjusted along the tendon by sliding to obtain the desired length. The bone blocks are secured in the respective tunnel by an interference screw which is inserted into the channel formed on the outside surface of the bone block opposite the longitudinal planar surface. The tendon replacement member is in turn secured to the two bone blocks by sutures. The use of the bone-tendon-bone composite graft of the invention results in a reconstructed tendon.

It is another object of the invention to utilize a shaped bone implant structure which approximates the mechanical strength characteristics of a natural cortical bone-tendon-bone to provide overall strength and initial durability to the structure.

It is also an object of the invention to provide a pre-machined bone derived structure which can effectively promote new bone growth and accelerate healing.

It is yet another object of the invention to create a bone-tendon-bone assembly which mimics the configuration of natural bone-tendon-bone constructs.

It is still another object of the invention to create a bone-tendon-bone assembly which can be easily handled by the physician during surgery which eliminates or significantly reduces the physician from carving the respective bone blocks.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention.

BRIEF DESCRIPTION OF THE DRAWINGS

FIG. 1 is a perspective view of the inventive art bone-tendon-bone implant;

FIG. 4 is a side elevational view of the inventive bone-tendon-bone assembly of FIG. 1;

FIG. 5 is a front elevational view of the inventive bone-tendon-bone assembly of FIG. 4 prior to implantation in a knee joint;

FIG. 6 is an enlarged side elevational of the inventive bone block;

FIG. 7 is a top plan of the bone block of FIG. 6; and

FIG. 8 is a sectional end view of the bone block of FIG. 6.

DETAILED DESCRIPTION OF THE INVENTION

Figure 3:
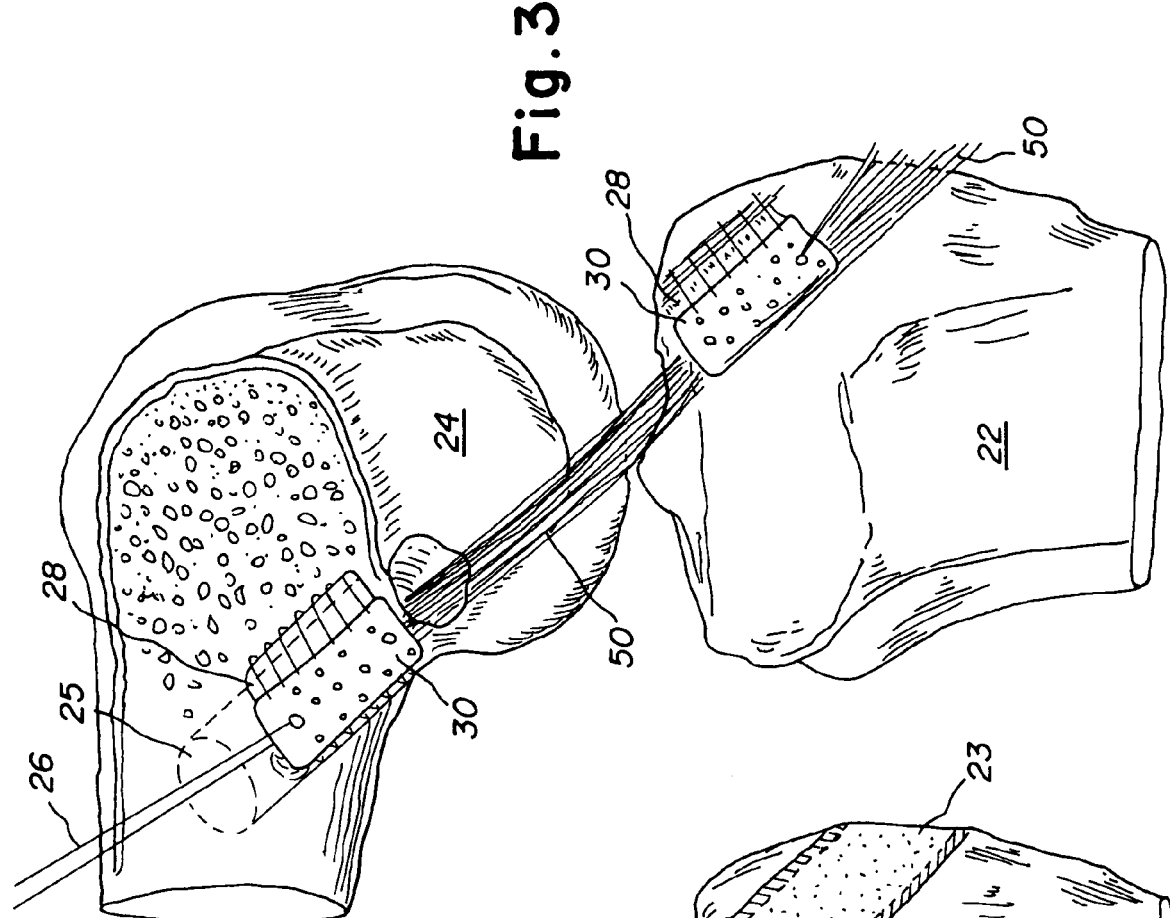
FIG. 3 is a perspective view of the inventive bone-tendon-bone assembly implanted and secured in a knee joint.
Figure 2:
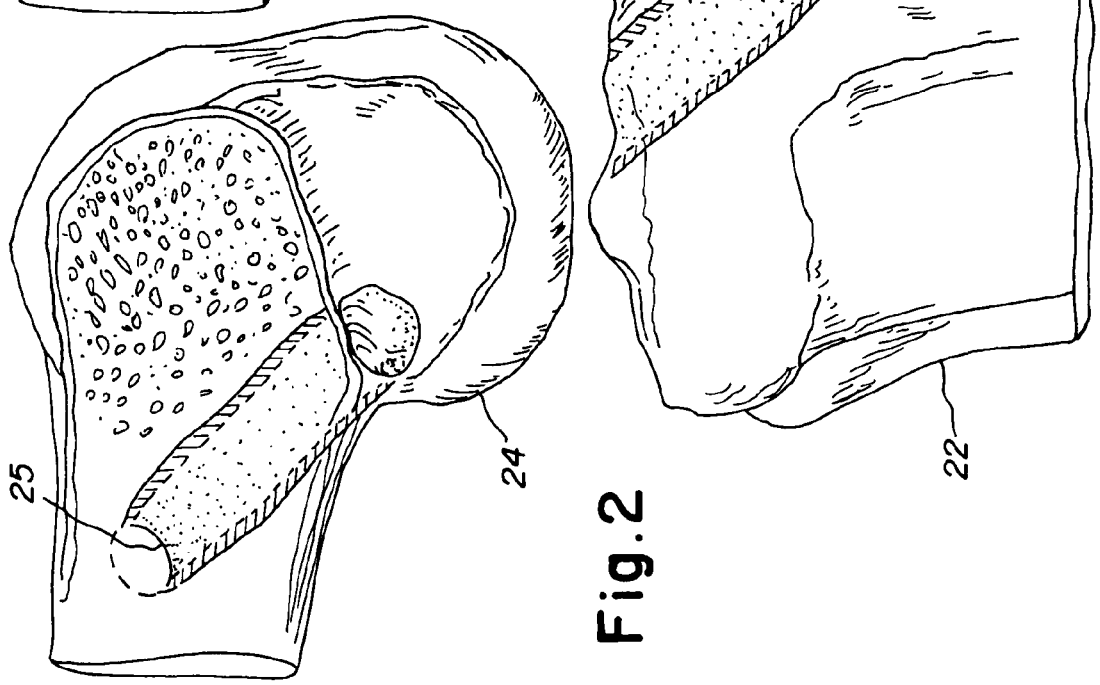
FIG. 2 is a view of the knee showing the tibia and femur with tunnels cut there through for implantation of the inventive implant.

The preferred embodiment and best mode of the present invention is shown in FIGS. 1 and 4-8.

As shown in the drawings, a reconstructed bone-tendon-bone (B-T-B) assembly 10 for a knee joint is shown in FIG. 1 in accordance with the present invention. The cruciate ligament reconstruction surgical operation can be conducted as an open orthopedic surgery or through arthroscopic surgery. While the description of the invention is primarily directed to knee reconstruction, the present invention can easily be adapted to other joints requiring ligament or tendon replacement.

A number of surgical methods and variation of the same can be used in the knee tendon reconstructive surgery. Representative methods which are exemplary but not exclusive or limited are referred to as the Lipscom et al. Technique, the Puddu Technique, the Zaricznyj Technique, the Zarins and Rower Techniques and are set forth and fully explained in Chapter 29, Knee Injuries, Campell's Orthopaedics (1998, 9 h Ed.) and are incorporated herein by reference. In most B-T-B procedures anteromedial and distal lateral bores are drilled to give access to the knee joint for these procedures.

In the standard ACL reconstruction, the intercondylar notch is prepared by drilling the femoral tunnel of the ACL. The tibial hole is prepared by drilling using a cannulated reamer of 8 mm to 12 mm diameter and the intra-articular fluid is drained. The cannulated system is used to place the tunnels anatomically over a guide wire in the tibial and femoral anatomy. The tibial tunnel entrance is midway between the tibial tubercle and the posterior medial edge of the proximal tibia, approximately 3 finger widths below the joint line. The exit for the tibia tunnel is the posterior medial footprint of the native ACL. With the knee positioned at 90 degrees of flexion, the guide pin is placed in the intercondylar notch and exits the superior lateral femur just above the flare of the condyle. The femoral tunnel is then placed using a cannulated reamer over the guide wire to accommodate a bone block. The graft is passed into position in the femoral tunnel and fixed with an interference screw.

The two major bones that meet at the knee joint are the tibia 22 and the femur 24. Bone tunnels 23 and 25 are drilled through each of these two bones 22, 24 respectively with a desired diameter. The tunnels 23 and 25 may be drilled with a regular drill that crushes and removes the bone within the tunnel but it is preferable to use a coring reamer to drill the bone tunnels. The reamer drills out a core of bone through each of the bone tunnels. The knee is flexed or extended a variable amount in order to properly position the femoral tunnel. The reamer is then directed through the tibial tunnel for drilling in and through the femur. The bone core from the femur is removed. Standard deburing and debridement procedures are followed.

For the purposes of the present invention, relative size relationships will be set forth which should not be constructed as forming specific size limitations. After the cores have been drilled out forming bone tunnels 23 and 25 with a standard 11 mm diameter, an allograft B-T-B assembly with pre-machined cancellous bone blocks 30 and an attached treated tendon member(s) 50 is inserted into the bone tunnels by pulling the respective bone blocks into the tunnels via sutures 26 as seen in FIG. 3 with the bone blocks being fixed in the tunnel by an interference screw 28. The interference screw 28 engages the bone block 30 and the tibia and/or femur to hold the tendon 50 in place. The general OD of the bone block and tendon is around 11 mm or the diameter of the bone tunnel allowing the same to be frictionally held in place prior to interference engagement with screw 28. The interference screw 28 is preferably 9 mm in thickness and it compresses and crunches the cancellous bone increasing the density of the bone until a pull out strength of over 200 Newtons is reached preferably in the range of 250-500 Newtons. The tendon(s) pass through the block central bore 32 and along a flat longitudinal surface 34 of the bone block. As can be seen in the figures, the sliding bone blocks are mounted on opposite tendon members or bundles in a reversed position. This opposite positioning balances the tendon bundle tension.

As can be seen in FIGS. 4-8, a cancellous bone block body 30 which is preferably constructed of denser cancellous bone or bone which is taken from younger donors is cut into a substantially cylindrical shape with an arc removed leaving a flat planar surface 34. If desired, the block body can be constructed of cortical bone which is partially demineralized, ceramics, xenograft bone or a bioabsorbable polymer. The curved outer surface 31 of the bone block body typically has a diameter ranging from 8 mm to 12 mm in diameter. The bone block 30 defines a central oval or oblong shaped through going bore 32 cut therethrough along the anatomical canal. The body 30 has a planar surface 34 cut into the outer surface 31 of the bone block which runs the length of the bone block to provide a surface for seating the looped tendon 50 and has a channel 36 cut into the opposite side of the bone block for inserting an interference fixation screw 28 to hold the bone block 30 in place in the tunnel. The channel 36 which receives the fixation screw 28 is oppositely positioned from the channel of the other block when the bone-tendon-bone assembly is attached and faces outwards from the assembly. As previously noted the bone block diameter can vary from 8-12 mm with a corresponding length of 25-35 mm depending upon surgeon preference and the diameter of the bone tunnels being used. An end bevel or angle 33 as most clearly shown in FIG. 6 is cut into the end of the bone block body 30 to allow easier insertion into the bone tunnel and to provide a flush alignment of the bone block with the articulating end of the tunnel at both the tibial and femoral placement. This beveled end will minimize the contact between the bone block and the articulating cartilage on the faces of the knee joint. The femoral angle will preferably have a range from 5 to 15 degrees and tibial angle from 15 to 30 degrees. Suture holes 37 are radially cut through the bone block with an axis parallel to the planar surface 34 located 90° from channel 36 and lead into the central bore 32 for attaching the tendon(s) 50 to the bone block 30 via sutures 26. In the preferred embodiment, at least two such suture holes 37 are drilled through the bone block. The sutures 26 are also used to pull the respective bone block into the desired location in tunnels 23 and 25 and to adjust the same to the desired length The pre-drilled suture holes in the bone face are located at the bone face at a location so as not to have the suture 26 cut by the interference screw 28 which is directed along channel 36. In addition, a plurality of circulation holes can be cut radially into the surface of the bone block body leading from the outer surface 31 to the central core 32 to expose the interior of the bone block and allow faster bone growth if desired. These circulation holes would preferably have a diameter of 1 mm or less.

The inventive design also provides a significantly thinner bone block cross-sectional diameter. This is critical during the entry and proper placing of the bone block in the tunnel drilled by the surgeon. Thus the tendon is placed in an specific orientation relative to the bone block with the positional orientation of the bone blocks on the tendon being reversed from each other although still having the screw channel 36 located outside of the tendon with planar surface 34 being adjacent the tendon.

When using multiple strands of tendons 50, as an example, a semitendinosus tendon and/or gracilis tendon are extended between both of the bone blocks 30, 130. The tendon(s) 50 are preferably sutured to themselves after positioning of the blocks in the bone tunnels to form a double loop as shown in FIGS. 4 and 5. Sutures 26 are also used through the suture holes 37 to attach the tendon(s) to each of the bone blocks and sutures 126 are used to connect the tendon loops after the blocks have been positioned as seen in FIGS. 1, 3 and 4. The tendon or ligament replacement of an embodiment of the invention may include one or more of the following tendons: patellar, semitendinosus, gracilis, quadriceps, adductor magnus, the hamstrings, peroneus longus and hallucis longus. The tendons typically run from 180 mm to 200 mm in length and when harvested are fresh frozen or freeze dried after cleaning for preservation for use in the B-T-B assembly. The tendon can be sterilized with radiation dosages as is well known in the art. As such the tendon structure or member combining one or more of the above noted tendons will connect the two bone blocks. Single bone blocks can be used with the Achilles, biceps femoris and quadriceps tendons as these come naturally with a bone block.

Still further embodiments of the invention may substitute or combine man made or artificial fibers or human tissue for the tendons for use as the ligament replacement. After the bone blocks have been inserted in the bone tunnels, the sutures 26 hanging from one end of the composite graft are attached to a needle, a passer or other conventional graft placement tool.

The proper tension is then applied to the graft by pulling on the suture 26 hanging out from the tibial incision. A driver and a headless interference screw 28 are then inserted through the tibial incision for driving the screw along the channel 36 of the bone block crushing the cancellous bone and anchoring the bone block in place. The second block is then slid on the tendon 50 until the desired position is reached and it is screwed into place. In affixing the composite graft 10 within a bone tunnel, contact between an interference screw 28 and the tendon 50 should be avoided so as not to cut or tear the tendon which is why the tendon is located on flat surface 34 opposite the channel 36. In order to also insure that the screw is out of contact with the tendon and the sutures, the interference screw 28 should be driven along the bone portion of the bone block channel 36 and the respective bone tunnel wall. The sutures 26 are then cut and the incisions are closed.

It is believed that a safety factor of 200 Newtons should be the minimum standard for pull out force even though staples are currently being used by some medical graft providers with a 50 Newtons pull out force. The bone blocks with tendon has been tested on human cadavers and found to have surprising pull out strength. Column 1 reflects the donor in which the bone tunnel was drilled; the second donor reflects the bone block source and the third donor the tendon source. The testing was all cadaver testing to reflect real life conditions and comparable research testing using porcine bone (much denser than human bone) and sawbone (also denser) would show higher pull out strength, ranging from 10% to 25% on average. It should also be noted that the same tibia donor was used in tests No. 12 and 13. This tibia was found to be porous and in a deteriorated condition one might expect to find in a much older woman. The load failure in Newtons is shown on the following table.

Testing Summary

| TEST # | Prox. Tibia Donor # | Donor Age/Sex | Bone Block Donor # | Tissue Source Age/Sex | Tendon Source | Donor # Age/Sex | Load @ Failure N |
|---|---|---|---|---|---|---|---|
| 1 | #00826455 | 42/F | #00314711 CORTICAL | Fibula 36/F | Semi-T | #01722632 29/M | 255N |
| 2 | #00819209 | 39/M | #02316000 CORTICAL | Fibula 54/M | Tibialis P | #03225561 50/M | 260N |

-continued

Testing Summary

| TEST # | Prox. Tibia Donor # | Donor Age/Sex | Bone Block Donor # | Tissue Source Age/Sex | Tendon Source | Donor # Age/Sex | Load @ Failure N |
|---|---|---|---|---|---|---|---|
| 3 | #00713606 | 49/M | #00314711 CORTICAL | Fibula 36/F | Semi-T | #01722632 29/M | 282N |
| 4 | #00184080 | 57/F | #00323480 Cancellous | U-C Dowel 58/M | Tibialis P | #01725932 36/M | 360N |
| 5 | #03614081 Left | 47/F | #00323480 Cancellous | U-C Dowel 58/M | Tibialis P | #01725932 36/M | 380N |
| 6 | #00522107 | 51/F | #00323480 Cancellous | U-C Dowel 58/M | Tibialis A | #03225561 50/M | 505N |
| 7 | #03614081 Right | 47/F | #03828534 Cancellous | Talus 44/M | Tibialis A | #03530011 46/M | 324N |
| 8 | #00819822 | 26/F | #03828534 Cancellous | Talus 44/M | Tibialis A | #03530011 46/M | 244N |
| 9 | #00826455 | 42/F | #03828534 Cancellous | Calcaneus 44/M | Tibialis A | #03328844 19/M | 363N |
| 10 | #03828461 Left | 55/M | #03828534 Cancellous | Calcaneus 44/M | Tibialis A | #03328844 19/M | 403N |
| 11 | #03828461 Right | 55/M | #00827347 Cancellous | Fem. Head 52/F | Semi-T | #02124998 43/M | 395N |
| 12 | #00327886 Left | 34/F | #00827347 Cancellous | Fem. Head 52/F | Semi-T | #02124998 43/M | 236N |
| 13 | #00327886 Right | 34/F | #03828534 Cancellous | Calcaneus 44/M | Semi-T | #00327886 34/F | 284N |

While this operation has been discussed in terms of using the preferred embodiment allograft cancellous bone blocks, alternative sources of bone blocks may be substituted such as cortical bone blocks, xenograft bone or synthetic graft materials such as ceramics or plastics such as bioabsorbable polymers. With any of these alternatives, the bone blocks may be shaped as described above for the graft.

The unique features of bone that make it desirable as a surgical material are, its ability to slowly resorb and be integrated into the space it occupies while allowing the bodies own healing mechanism to restore the repairing bone to its natural shape and function by a mechanism known in the art as creeping substitution. The second feature is the high mechanical pull out strength arising from the crushed bone structure and collagen fiber. Thus a means of accelerating the rate of biointegration of cancelleous bone would improve the rate of healing and benefit the recipient patient. The bone blocks may also be partially demineralized to increase osteoinductiveness.

It is well known that bone contains osteoinductive elements known as bone morphogenetic proteins (BMP). These BMP=s are present within the compound structure of cortical bone and are present at a very low concentrations, e.g. 0.003%. The BMP's are present in higher concentrations in cancellous bone. BMP's direct the differentiation of pluripotential mesenchymal cells into osteoprogenitor cells which form osteoblasts. The ability of freeze dried demineralized bone to facilitate this bone induction principle using BMP present in the bone is well known in the art. However, the amount of BMP varies in the bone depending on the age of the bone donor and the bone processing. Based upon the work of Marshall Urist as shown in U.S. Pat. No. 4,294,753, issued Oct. 13, 1981 the proper demineralization of cortical bone will expose the BMP and present these osteoinductive factors to the surface of the demineralized material rendering it significantly more osteoinductive. The removal of the bone mineral leaves exposed portions of collagen fibers allowing the addition of BMP's and other desirable additives to be introduced to the demineralized outer treated surface of the bone structure and thereby enhances the healing rate of the cortical bone in surgical procedures. In cancellous bone the structure is not as dense as cortical bone exposing the naturally occurring BMP's rendering the entire structure with biological properties similar to fully demineralized bone (DBM).

The bone blocks of the present invention were prepared by machining cancellous bone from younger donors in the ranges shown in the present tables which have a denser cancellous structure. Suitable bones are calcaneus patella, femoral head, long bone condyles and talus.

It is also possible to add one or more rhBMP's to the bone by soaking and being able to use a significantly lower concentration of the rare and expensive recombinant human BMP to achieve the same acceleration of biointegration. The addition of other useful treatment agents such as vitamins, hormones, antibiotics, antiviral and other therapeutic agents could also be added to the bone.

Any number of medically useful substances can be incorporated in the bone block and tendon assembly by adding the substances to the assembly. Such substances include collagen and insoluble collagen derivatives, hydroxyapatite and soluble solids and/or liquids dissolved therein. Also included are antiviricides such as those effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin, gentamycin and silver salts. It is also envisioned that amino acids, peptides, vitamins, co-factors for protein synthesis; hormones; endocrine tissue or tissue fragments; synthesizers; enzymes such as collagenase, peptidases, oxidases; polymer cellpl scaffolds with parenchymal cells; angiogenic drugs and polymeric carriers containing such drugs; collagen lattices; biocompatible surface active agents, antigenic agents; cytoskeletal agents; cartilage fragments, living cells, cell elements such as chondrocytes, red blood cells, white blood cells, platelets, blood plasma, bone marrow cells, mesenchymal stem cells, pluripotential cells, osteoblasts, osteoclasts, fibroblasts, epithelial cells and entothial cells, natural extracts, tissue transplants, bioadhesives, transforming growth factor (TGF-beta), insulin growth factor (IGF-1), platelet derived growth factor (PDGF), fibroblast growth factor (FGF)(Numbers 1-23), platelet derived growth factor (PDGF), vascular endothelial growth factor (VEGF), osteopontin; growth hormones such as somatotropin; cellular attractants and attachment agents; fibronectin; immunosuppressants; permeation enhancers, e.g. fatty acid esters such as laureate, myristate and stearate monoesters of polyethylene glycol, enamine derivatives, alpha-keto aldehydes can be added to the composition.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What is claimed is:

1. A sterile bone-tendon-bone assembly comprising: a first biocompatible bone block defining an outer curved surface, a central throughgoing bore having a cross section which will allow a tendon replacement member to be passed therethrough and a longitudinal channel cut in its outer exterior surface; an exterior surface of said bone block positioned away from said channel forming a planar surface, a tendon replacement member extending through said central throughgoing bore of said bone block; a second biocompatible bone block having the same construction as the first bone block with said tendon replacement member extending through said central bore of said second bone block, said second bone block being in reversed orientation to said first bone block with the channels of said bone blocks being positioned so that they do not engage said tendon replacement member.

2. A sterile bone-tendon-bone assembly as claimed in claim 1 wherein said first and second bone blocks central through going bore has a substantially oval cross section and each block further includes at least one suture hole drilled radially through each of said bone blocks spaced away from said longitudinal channel through to the central bore.

3. A sterile bone-tendon-bone assembly as claimed in claim 1 wherein said first and second bone blocks are constructed of allograft cancellous bone.

4. A sterile bone-tendon-bone assembly as claimed in claim 3 wherein said first and second bone block constructed of allograft cancellous bone are taken from a group of bones consisting of a cancellous patella, femoral head, long bone condyles and talus.

5. A sterile bone-tendon-bone assembly as claimed in claim 3 wherein said first and second bone block are taken from a group of bones consisting of a cancellous patella, femoral head, long bone condyles and talus.

6. A sterile bone-tendon-bone assembly as claimed in claim 1 wherein said first and second bone blocks are constructed of ceramic.

7. A sterile bone-tendon-bone assembly as claimed in claim 1 wherein said first and second bone blocks are constructed of bioabsorbable polymers.

8. A sterile bone-tendon-bone assembly as claimed claim 1 wherein at least one bone block includes an additive taken from a group of additives consisting of living cells, chondrocytes, red blood cells, white blood cells, platelets, blood plasma, bone marrow cells, mesenchymal stem cells, pluripotential cells, osteoblasts, osteoclasts, fibroblasts, epithelial cells and entothial cells, natural extracts, tissue transplants, and growth factors consisting of transforming growth factor (TGF-beta), insulin growth factor (IGF-1), platelet derived growth factor (PDGF), fibroblast growth factor (FGF)(Numbers 1-23), platelet derived growth factor (PDGF),vascular endothelial growth factor (VEGF), osteopontin; somatotropin; and growth hormones.

9. A sterile bone-tendon-bone assembly as claimed in claim 1 wherein at least one of said bone blocks is constructed of ceramic.

10. A sterile bone-tendon-bone assembly as claimed in claim 1 wherein said tendon replacement member comprises at least one tendon taken from a group of tendons consisting of a semitendinous tendon, a patellar tendon, gracilis tendon, quadriceps tendon, adductor magnus tendon, peroneus tendons, tibialis tendons and hallucis Achilles tendon.

11. A sterile bone-tendon-bone assembly as claimed in claim 1 wherein at least one bone block is constructed of xenograft bone.

12. A sterile bone-tendon-bone assembly as claimed in claim 1 wherein at least one bone block is constructed of allograft bone.

13. A sterile bone-tendon-bone assembly as claimed in claim 1 wherein said tendon replacement member comprises a semitendinosus tendon.

14. A sterile bone-tendon-bone assembly as claimed in claim 1 wherein said tendon replacement member comprises a patellar tendon.

15. A sterile bone-tendon-bone assembly as claimed in claim 1 wherein said tendon replacement member comprises a gracilis tendon.

16. A sterile bone-tendon-bone assembly as claimed claim 1 wherein said bone block includes an additive taken from a group of additives consisting of living cells, cell elements such as chondrocytes, red blood cells, white blood cells, platelets, blood plasma, bone marrow cells, mesenchymal stem cells, pluripotential cells, osteoblasts, osteoclasts, fibroblasts, epithelial cells and entothial cells, natural extracts, and tissue transplants.

17. A sterile bone-tendon-bone assembly as claimed in claim 1 wherein each bone block includes an additive taken from a group of additives consisting of transforming growth factor (TGF-beta), insulin growth factor (IGF-1), platelet derived growth factor (PDGF), fibroblast growth factor (FGF)(Numbers 1-23), platelet derived growth factor (PDGF),vascular endothelial growth factor (VEGF), osteopontin, somatotropin, and growth hormones.

18. A sterile bone-tendon-bone assembly comprising: first and second substantially cylindrical allograft cancellous bone blocks, each bone block defining a central through going bore, a channel cut in its outer surface and a longitudinal planar surface cut on the opposite side of said bone block from said channel, a tendon replacement member extending between said first and second bone blocks through said central bore, and seated over said planar surface alongside each of said first and second bone blocks and at least one suture hole cut transverse to said central bore away from said channel and intersecting said central bore; said second bone block being in a reversed orientation of said first bone block with said channel being positioned on the outside of said assembly.

19. A sterile bone-tendon-bone assembly as claimed in claim 18 wherein said tendon replacement member comprises a first tendon replacement strand and a second tendon replacement strand.

20. A sterile bone-tendon-bone assembly as claimed in claim 18 wherein said tendon replacement member comprises a plurality of strands.

21. The sterile bone-tendon-bone assembly of claim 20 wherein at least one of said tendon replacement strands is xenograft tissue.

22. The sterile bone-tendon-bone assembly of claim 20 wherein said at least one of said tendon replacement strands is allograft tissue.

23. A sterile bone-tendon-bone assembly of claim 20 wherein said tendon replacement strands comprise at least one tendon taken from a group of tendons consisting of a semitendinous tendon, a patellar tendon, gracilis tendon, quadriceps tendon, adductor magnus tendon, peroneus tendons, tibialis tendons and hallucis Achilles tendon.

24. A sterile bone-tendon-bone assembly as claimed claim 18 wherein each bone block includes an additive taken from a group of additives consisting of living cells, cell elements such as chondrocytes, red blood cells, white blood cells, platelets, blood plasma, bone marrow cells, mesenchymal stem cells, pluripotential cells, osteoblasts, osteoclasts, fibroblasts, epithelial cells and entotbial cells, natural extracts, and tissue transplants.

25. A sterile bone-tendon-bone assembly as claimed in claim 18 wherein each bone block includes an additive taken from a group of additives consisting of transforming growth factor (TGF-beta), insulin growth factor (IGF-1), platelet derived growth factor (PDGF), fibroblast growth factor (FGF)(Numbers 1-23), platelet derived growth factor (PDGF),vascular endothelial growth factor (VEGF), osteopontin, growth hormones such as somatotropin.

26. A sterile bone-tendon-bone assembly as claimed in claim 18 wherein said bone block is constructed of allograft bone which is partially demineralized.

27. A sterile reconstructed cruciate tendon assembly comprising: first and second allograft substantially cylindrical bone blocks; each bone block comprising a body of cancellous bone with a central through going bore, a channel cut in the outer surface of said substantially cylindrical body and a flat surface forming a cord cut into the outer surface of substantially cylindrical body opposite said channel, a tendon replacement strand extending between said first and second bone blocks is inserted through said central bore and attached longitudinally alongside each of said first and second bone blocks adjacent said flat surface with said first and second bone blocks each having at least one suture hole extending radially through said bone block from said central bore through to an outer surface and said bone blocks have an angled beveled end surface, said second allograft bone block being positioned on said tendon replacement member in a reversed position from said first allograft bone block.

28. A sterile bone-tendon-bone assembly as claimed in claim 27 wherein said tendon replacement member comprises a plurality of strands.

29. The sterile bone-tendon-bone assembly of claim 28 wherein at least one of said tendon replacement strands is xenograft tissue.

30. The sterile bone-tendon-bone assembly of claim 28 wherein said at least one of said tendon replacement strands is allograft tissue.

31. A sterile bone-tendon-bone assembly of claim 27 wherein said tendon replacement strands comprise at least one tendon taken from a group of tendons consisting of a semitendinous tendon, a patellar tendon, gracilis tendon, quadriceps tendon, adductor magnus tendon, peroneus tendons, tibialis tendons and hallucis Achilles tendon.

32. A method of inserting a bone-tendon-bone assembly in a joint comprising the steps of:
  a) cutting a bone tunnel in each of two bones of a joint;
  b) placing a bone block of bone-tendon-bone assembly comprising a first biocompatible bone block defining an outer curved surface, a central through going bore having a cross section which will allow a tendon replacement member to be passed therethrough and a longitudinal channel cut in its outer exterior surface; an exterior surface of said bone block positioned away from said channel forming a planar surface, a tendon replacement member extending through said central throughgoing bore of said bone block, a second biocompatible bone block having the same construction as the first bone block with said tendon replacement member extending through said central bore of said second bone block, said second bone block being in reversed orientation to said first bone block with the channels of said bone blocks being positioned so that they do not engage said tendon replacement member;
  c) sliding the bone blocks along the tendon replacement member until the correct length for support and flexure is reached;
  d) fastening the bone blocks in place on the tendon replacement member; and
  e) sequentially fastening each bone block in place in a bone tunnel cut in each of said two bones of a joint.

33. A method of inserting a bone-tendon-bone assembly as claimed in claim 32 wherein said fastening step comprises inserting an interference screw into said bone block channel and a side wall of a bone tunnel.

34. A method of inserting a bone-tendon-bone assembly as claimed in claim 32 wherein said placing step comprises inserting a suture through holes cut in said bone block and pulling said bone block into a bone tunnel.

35. A method of inserting a bone-tendon-bone assembly as claimed in claim 32 wherein a first bone block is fastened in place on a tendon replacement member and then fastened in said bone tunnel prior to the second bone block being fastened in place on said tendon replacement member.

* * * * *